(12) United States Patent
Schueth et al.

(10) Patent No.: US 9,844,774 B2
(45) Date of Patent: Dec. 19, 2017

(54) PROCESS FOR PREPARING CATALYST LOADED POLYPHENYLENE PARTICLES, THE OBTAINED POLYPHENYLENE PARTICLES AND THEIR USE AS CATALYSTS

(71) Applicant: STUDIENGESELLSCHAFT KOHLE MBH, Mülheim an der Ruhr (DE)

(72) Inventors: Ferdi Schueth, Mülheim an der Ruhr (DE); Alois Fürstner, Mülheim an der Ruhr (DE); Feng Wang, Mülheim an der Ruhr (DE)

(73) Assignee: STUDIENGESELLSCHAFT KOHLE MBH, Muelheim an der Ruhr (DE)

( * ) Notice: Subject to any disclaimer, the term of this patent is extended or adjusted under 35 U.S.C. 154(b) by 0 days.

(21) Appl. No.: 15/300,823

(22) PCT Filed: Mar. 24, 2015

(86) PCT No.: PCT/EP2015/056315
§ 371 (c)(1),
(2) Date: Sep. 30, 2016

(87) PCT Pub. No.: WO2015/150173
PCT Pub. Date: Oct. 8, 2015

(65) Prior Publication Data
US 2017/0021342 A1    Jan. 26, 2017

(30) Foreign Application Priority Data
Mar. 31, 2014  (EP) ..................................... 14162958

(51) Int. Cl.
| | | |
|---|---|---|
| C07C 51/00 | (2006.01) |
| C08G 61/00 | (2006.01) |
| B01J 31/00 | (2006.01) |
| B01J 31/06 | (2006.01) |
| C07C 1/32 | (2006.01) |
| C07C 45/38 | (2006.01) |
| B01J 23/44 | (2006.01) |
| B01J 37/04 | (2006.01) |
| B01J 37/16 | (2006.01) |
| C07C 41/30 | (2006.01) |
| C07C 51/255 | (2006.01) |
| C08G 61/10 | (2006.01) |

(52) U.S. Cl.
CPC ............... *B01J 31/06* (2013.01); *B01J 23/44* (2013.01); *B01J 37/04* (2013.01); *B01J 37/16* (2013.01); *C07C 1/321* (2013.01); *C07C 41/30* (2013.01); *C07C 45/38* (2013.01); *C07C 51/255* (2013.01); *C08G 61/10* (2013.01); *B01J 2231/4211* (2013.01); *C07C 2523/42* (2013.01); *C07C 2531/02* (2013.01); *C07C 2531/06* (2013.01); *C07C 2531/28* (2013.01); *C08G 2261/11* (2013.01); *C08G 2261/312* (2013.01); *C08G 2261/79* (2013.01); *C08G 2261/90* (2013.01)

(58) Field of Classification Search
CPC ........ C07C 51/255; C08G 61/10; B01J 31/06; B01J 23/44
See application file for complete search history.

(56) References Cited

U.S. PATENT DOCUMENTS 3,974,095 A    8/1976  Volpin et al.

OTHER PUBLICATIONS

Chen et al., "Light-Harvesting Conjugate Microporous Polymers: Rapid and Highly Efficient Flow of Light Energy with a Porous Polyphenylene Framework as Antenna"; J. Am. Chem. Soc., 2010, vol. 132, pp. 6742-6748.
Karami, et al.; "Palladium nanoparticles supported on polymer: An efficient and reusable heterogenous catalyst for the Suzuki cross-coupling reactions and aerobic oxidation of alcohols"; Catalysis Communications; vol. 38, 2013, pp. 10-15.
Richter, et al.; "Structural mimicking of inorganic catalyst supports with polydivinylbenzene to improve performance in the selective aerobic oxidation of ethanol and glycerol in water"; Journal of Catalysis, vol. 308, 2013; pp. 341-351.

*Primary Examiner* — Sikarl Witherspoon
(74) *Attorney, Agent, or Firm* — Norris McLaughlin & Marcus, P.A.

(57)    ABSTRACT

The present invention refers to processes for preparing catalyst loaded polyphenylene particles, the so-obtained polyphenylene particles and their use as catalysts.

19 Claims, 8 Drawing Sheets

Figures 8 a, b

Physisorption of DiBB-Phenyl and DiBB/TetraBB-Phenyl

PROCESS FOR PREPARING CATALYST LOADED POLYPHENYLENE PARTICLES, THE OBTAINED POLYPHENYLENE PARTICLES AND THEIR USE AS CATALYSTS

This application is a 371 of PCT/EP2015/056315, filed Mar. 24, 2015, which claims foreign priority benefit under 35 U.S.C. §119 of European Patent Application No. 14162958.4, filed Mar. 31, 2014, the disclosures of which patent applications are incorporated herein by reference.

The present invention refers to processes for preparing catalyst-loaded polyphenylene particles, the so-obtained polyphenylene particles and their use as catalysts in various chemical processes.

Solid catalysts have important advantages compared to molecular systems, such as easier separation and better recyclability. Nevertheless, 90% of the processes in the fine chemical and pharmaceutical industry are homogeneous due to the difficulties in finding suitable solid catalysts. A major goal in catalysis is to combine the advantages of molecular catalysts and heterogeneous processes, in order to maintain—or even improve—the reactivity and selectivity of the molecular catalysts, and to facilitate product recovery and catalyst recycling. This may allow processes which are currently difficult or impossible, if molecular catalysts are used.

Due to their suitability for continuous processes in fixed bed reactors, solid catalysts are used in ~75% of all catalytic processes for the synthesis of bulk chemicals. However, they are less frequently employed for the production of fine-chemicals or pharmaceutical molecules, due to the fact that many of the traditional organic reactions require a nonpolar or less polar environment for which the typical solid catalysts, based on oxide support materials, are not the ideal choice. A suitable organic environment for such reactions is more readily realized with metal complexes and suitable ligands and solvents, which provide the required geometry and stabilize the transition state of the reaction.

Typical inorganic supports provide neither ligand effects nor a solvent-like environment, which often leads to reduced activity of solid catalysts for the chemical transformations commonly required in the production of fine chemicals. In contrast, polymeric supports, such as polyalkenes or polyethers, have low polarity and can increase the support-reactant/substrate interactions, which have first been demonstrated in the synthesis of peptides and proteins. The polymers create a 'solvent'-like organic reaction environment, onto which ligands and metal complexes can be grafted to provide the catalytic functionality. Polymeric solids based on polystyrene, polydivinylbenzene (PDVB), polyacrylate derivatives, covalent organic frameworks (COF) or hybrid metal-organic frameworks have also been recently explored as carriers for catalytic metal nanoclusters and nanoparticles.

Nevertheless, practical applications of polymeric catalyst supports are to date limited to ion-exchange resin catalysts, since polymers do not offer the typical advantages of inorganic materials, such as high thermal stability and resilience to mechanical stress. Moreover, many inorganic supports provide synergistic effects due to metal-support interactions, and loading of the active component by impregnation or deposition-precipitation are well established synthetic methods for these supported catalysts.

At present, carbon materials are most widely applied when an apolar carrier material is required to host metal catalytic functionalities. Cross-linked 3D polymers, comprising aliphatic and aromatic building units, represent partially hydrogenated structural analogs to carbon materials. The presence of hydrogen atoms on their surface improves notably their capacity to establish synergistic interactions with organic reactant molecules in the vicinity of the catalytic species. However, they display a much lower thermal and mechanical stability than carbon counterparts, restricting their application in catalysis.

According to the inventors, an intermediate situation is realized in polyphenylene (PPhen) and all the carbon atoms are $sp^2$ hybridized in this polymer. The thermal and chemical stability of M-PPhen (M=metal) is higher than those of polymers that contain aliphatic parts, while M-PPhen still preserves the ability to serve as 'solvent' in reactions due to the presence of hydrogen atoms in its structure.

Polyphenylenes as catalysts for hydrogenation, isomerization and hydrosilylation of alkenes having 2-16 carbon atoms in the molecule, have been manufactured in U.S. Pat. No. 3,974,095 by polycyclotrimerization of p-diethynilbenzene or from ketals or acetals by acetylene substitution of benzene and subsequent loading with Pd, Pt, Ru and Rh as active metals. The copolymerization of diethynilbenzene with different derivatives of acetylene permits the introduction, into the polyphenylenes, of different functional groups to modify the properties of the polyphenylenes. This proves to be important when using polyphenylenes as ligands in catalytic systems.

Light-harvesting conjugated microporous polymers with a porous polyphenylene framework as antenna providing a rapid and highly efficient flow of light energy are described by Long Chen and Coworkers in J. AM. CHEM. SOC. 2010, 132, 6742-6748. The PPhen as prepared discloses amount of Pd as a remainder of the used catalyst in the PPhen structure. The publication focuses on the microporous structure of PP-CMP to allow for the spatial confinement of energy-accepting coumarin 6 molecules in the pores and to make the high-throughput synthesis of light-harvesting systems with designable donor-acceptor compositions possible. There is no mentioning of any catalytic activity of said PPhen structure in said publication.

In contrast, PPhen has been found by the inventors to serve as an ideal catalyst support platform for fine chemical synthesis. Thus, the present invention presents a catalyst comprised of metal nanoparticles such as palladium nanoparticles supported on a porous PPhen network synthesized, in one embodiment of the invention, by cross-coupling reactions, such as coupling between 1,2,4,5-tetrabromobenzene and benzene-1,4-diboronic acid as shown in FIG. 1.

The catalyst-loaded polyphenylene particles of the present invention can be synthesized by a palladium catalyzed Suzuki coupling reaction between di-, tri- or tetrabromo-aryl compounds with corresponding di-, tri or tetraboronic acid aryl-compounds, or preferably stoichiometric mixtures thereof, which directly results in the formation of palladium nanoparticles confined to a porous polyphenylene network. The as-synthesized catalyst is in turn highly active for further Suzuki coupling reaction.

The present invention is therefore directed to a catalyst loaded, particularly metal loaded polyphenylene polymer particles which are preferably obtainable by a Suzuki coupling reaction of a polyhalo-aryl compound, such as di-, tri or tetrahalo-aryl compounds or mixtures thereof, with corresponding poly boronic acid aryl compounds, such as di-, tri or tetraboronic acid aryl-compounds or mixtures thereof, in the presence of a palladium phosphine compound and a base.

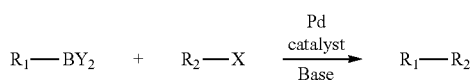

As the present invention allows preparing various catalyst-loaded polyphenylene polymer particles having nanoparticles of the catalytically active material dispersed in the polymer network, the present invention covers said catalyst-loaded polyphenylene polymer very generally. Such said catalyst nanoparticles are preferably having a particle size from 0.25 to 10 nm, preferably 0.25 to 8 nm, more preferably 0.25 to 6 nm, even more preferably from 0.25 to 5 nm, and even most preferably 0.25 to 4 nm, and the catalytically active material being selected from the group consisting of metals selected from Ti, V, Cr, Mn, Fe, Co, Ni, Cu, Zn, Al, Mo, Se, Sn, Pt, Ru, Pd, W, Ir, Os, Rh, Nb, Ta, Pb, Bi, Au, Ag, Sc, Y and alloys thereof, and compounds thereof wherein said compounds are selected from oxides, phosphides, nitrides or sulfides.

In the inventive catalyst-loaded polyphenylene polymer particles, the catalytically active material may be a metal which is preferably selected from the group consisting of Co, Ni, Pt, Ru, Pd, Ag, Au and alloys thereof.

The inventive catalyst-loaded polyphenylene polymer particles are generally containing said nanoparticles from 0.25 to 15%-by weight, preferably 2.5 to 10%-by weight based on the total weight of the polymer.

If the catalyst-loaded polyphenylene polymer particles are loaded with metals selected from Ti, V, Cr, Mn, Fe, Co, Ni, Cu, Zn, Al, Mo, Se, Sn, Pt, Ru, Pd, W, Ir, Os, Rh, Nb, Ta, Pb, Bi, Au, Ag, Sc, Y and alloys thereof, the catalyst-loaded polyphenylene polymer particles are obtainable in a first step by a Suzuki coupling reaction of di-, tri or tetrahalo-aryl compounds with di-, tri or tetraboronic acid aryl-compounds in the presence of a palladium phosphine compound and a base, whereby the molar ratio of the halogen-aryl compound to the boronic acid aryl-compound is preferably stoichiometric, depending on the number of the reacting halogens and the boronic acid groups, and might preferably be in the range of 2.5:1.0 to 1.0:2.5, preferably 2.0:1.0 to 1.0:2.0, and even more preferred 1.5:1.0 to 1.0:1.5. If the Pd is to be replaced by another metal as exemplified before, then removing the Pd from the PPhen network is the next step so that metal-free polyphenylene polymer particles remain.

In a second step, said catalyst-loaded polyphenylene polymer particles are obtainable by impregnating said metal-free polyphenylene polymer particles with a solution of a metal compound, preferably an organo metal complex or metal salt, and evaporating the solvent and converting the metal into the active form, if needed. Metal-free polyphenylene polymer particles means here that said particles are essentially free of Pd as the catalytical metal which has been used as catalyst for preparing the polyphenylene network by way of the Suzuki coupling reaction in the presence of a palladium salt.

Accordingly, the preferred process for preparing catalyst-loaded polyphenylene polymer particles comprises a first process step wherein di-, tri or tetrahalo-aryl compounds or mixtures thereof are reacted with di-, tri or tetraboronic acid aryl-compounds in the presence of a palladium compound and a base in a temperature range of 130° C. to 250° C. in a Suzuki coupling reaction whereby the molar ratio of the halogen-aryl compound to the boronic acid aryl-compound is preferably in the range of 2.5:1.0 to 1.0:2.5, preferably 2.0:1.0 to 1.0:2.0, and even more preferred 1.5:1.0 to 1.0:1.5.

In the process for preparing catalyst-loaded polyphenylene polymer particles, said di-, tri or tetrahalo-aryl-compounds are particularly selected from di-, tri- or tetrahalo-phenyl or -biphenyl compounds or mixtures thereof. Generally, aryl in the sense of the invention may be any aromatic hydrocarbon such a s phenyl, biphenyl, terphenyl, naphthyl, phenanthryl, anthracenyl and further condensed aromatic ring system or substituted derivatives thereof as long as they are capable of undergoing a Suzuki-coupling reaction in halo aryl partner or in boronic acid aryl partner.

In the process for preparing catalyst-loaded polyphenylene polymer particles, said di-, tri or tetraboronic acid aryl-compounds are preferably selected from di-, tri- or tetraboronic-acid phenyl or -biphenyl compounds or mixtures thereof.

Thus the preferred process for preparing catalyst-loaded polyphenylene polymer particles makes use of di-, tri or tetrabromophenyl or -biphenyl compounds or mixtures thereof being reacted with di-, tri or tetraboronic phenyl or -biphenyl compounds or mixtures thereof.

As pointed out above, the inventive process for preparing catalyst-loaded polyphenylene polymer particles can comprise the reaction steps wherein catalyst-loaded polyphenylene polymer particles are obtainable by impregnating metal-free polyphenylene polymer particles with a solution of a metal compound, preferably an organo metal complex or metal salt, and evaporating the solvent, and optionally converting the metal into the desired catalytically active metal compound wherein the metal is selected from Ti, V, Cr, Mn, Fe, Co, Ni, Cu, Zn, Al, Mo, Se, Sn, Pt, Ru, Pd, W, Ir, Os, Rh, Nb, Ta, Pb, Bi, Au, Ag, Sc, Y or alloys thereof.

By the inventive process, it is possible to prepare nearly any catalytically active compound to be dispersed in the polyphenylene polymer network if the metal free PPhen—metal free as explained above—is impregnated with a solution of such metal compound and then, in a second step, the metal compound is converted into the catalytically active species, if needed, before or after evaporation of the solvent of the solution of such metal compound.

Thus, the present invention discloses, for the first time, the use of a polyphenylene polymer network as a support for catalytically active compounds wherein the catalyst-loaded polyphenylene polymer particles are having nanoparticles of the catalytically active material dispersed in the polymer network which can be used as catalyst in a chemical process, wherein the catalytically active material is a metal is selected from Ti, V, Cr, Mn, Fe, Co, Ni, Cu, Zn, Al, Mo, Se, Sn, Pt, Ru, Pd, W, Ir, Os, Rh, Nb, Ta, Pb, Bi, Au, Ag, Sc, Y or alloys thereof, or compounds thereof wherein said compounds are selected from oxides, phosphides, nitrides or sulfides.

The chemical process wherein the catalyst-loaded polyphenylene polymer particles can be used is any process wherein the catalytic action can promote the chemical reaction. As examples, Suzuki coupling reactions or oxidation reactions, preferably as a gas phase reaction, are mentioned.

Due to the its stability, the catalyst-loaded polyphenylene polymer particles can be easily recycled from said catalytic process and reused in a further reaction cycle.

In a particular embodiment, the present invention refers to metal-loaded polyphenylene polymer particles having metal nanoparticles dispersed in the polymer network, said metal nanoparticles preferably having a particle size from 0.25 to 10 nm, preferably 0.25 to 8 nm, more preferably 0.25 to 6 nm, even more preferably from 0.25 to 5 nm, and even most preferably 0.25 to 4 nm, and the metal being selected from the group consisting of Ti, V, Cr, Mn, Fe, Co, Ni, Cu, Zn, Al, Mo, Se, Sn, Pt, Ru, Pd, W, Ir, Os, Rh, Nb, Ta, Pb, Bi, Au, Ag, Sc, Y and alloys thereof. The nanoparticles may be present in the form of nanocrystals, amorphous or nanoclusters, depending on the specific metal or its compound.

Besides metals, which might be obtainable after a hydrogenation step only, depending on the metal salt or metal compound used for impregnating, it is also possible to use metal compounds for impregnating which are finally present in the PPhen as oxide, phosphides, nitrides or mixtures of different metals or compounds.

Said metal nanoparticles are preferably having a particle size from 0.25 to 10 nm, preferably 0.25 to 8 nm, more preferably 0.25 to 6 nm, even more preferably from 0.25 to 5 nm, and even most preferably 0.25 to 4 nm all of which sizes are measured by electron microscopy. For a Pd nanoparticles loaded polymer, the size of the Pd nanoparticles may have a bimodal distribution with maximums between 0.5 and 1.5 nm and between 2.5 and 3.5 nm, preferably more than 50% of the particles having a particles size in the lower range between 0.5 and 1.5 nm.

The metal is preferably selected from the group consisting of Co, Ni, Pt, Ru, Pd, Ag and Au and alloys thereof, and the metal nanoparticles are present from 0.25 to 15%-by weight, preferably 2.5 to 10%-by weight based on the total weight of the polymer network.

In a preferred embodiment, the metal-loaded polyphenylene polymer particles are obtainable by said Suzuki coupling reaction of di-, tri or tetrahalo-aryl compounds with di-, tri or tetraboronic acid aryl-compounds in the presence of a palladium phosphine compound and a base, whereby the molar ratio of the halogen-aryl compound to the boronic acid aryl-compound is preferably in the range of 2.5:1.0 to 1.0:2.5, preferably 2.0:1.0 to 1.0:2.0, and even more preferred 1.5:1.0 to 1.0:1.5. In said reaction between the halogen-aryl compound and the boronic acid aryl-compound, the molar ratio of reacting halogen in the halogen-aryl compound to the boronic acid group in the boronic one compound should preferably be in the range of 0.8:1.2, preferably from 0.9:1.1 and most preferred equimolar. In said Suzuki reaction, the palladium phosphine compound is decomposed and precipitates into palladium nanoparticles which are embedded and confined inside the polymer solid network. Preferably, the reaction is carried out at a temperature range of 130° C. to 250° C. under a protective gas such as argon at ambient pressure and preferably in an inert organic solvent having a boiling point the range of 130° C. to 250° C., also in a polar organic solvent such as DMF. The choice of the solvent is not decisive as long as it does not negatively affect the reaction or reacts with any of the reagents.

In a further embodiment, the metal-loaded polyphenylene polymer particles are obtainable by impregnating metal-free polyphenylene polymer particles with a solution of a metal salt and evaporating the solvent. Said metal-free polyphenylene polymer particles can be obtained by carrying out the reaction as described before at a temperature of below 120° C., preferably at between 90° to 110° C. so that no decomposition of the metal catalyst, such as a palladium phosphine compound takes place and the catalyst will be washed off the polymer.

Said metal-free polyphenylene polymer particles can also be obtained by an oxidative leaching of the metal loaded polymer network, for example by treating the polymer with hydrogen peroxide in the presence of an inorganic acid such as hydrochloric acid.

In the next step after obtaining the essentially metal-free polymer network, the impregnation solution containing one soluble metal compound or mixtures of two or more metal compounds, such as metal salt of Ti, V, Cr, Mn, Fe, Co, Ni, Cu, Zn, Al, Mo, Se, Sn, Pt, Ru, Pd, W, Ir, Os, Rh, Nb, Ta, Pb, Bi, Au, Ag, Sc, Y, preferably, but no confined to their halogenides, nitrides, acetate, acetylacetonate and metal phosphine compounds, can be applied to the polymer network and, when increasing the temperature, the metal salt decomposes and the metal particles will be confined in the pores of the network and between the layers of the polyphenylene structure.

Preferably, the di-, tri or tetrahalo-aryl-compounds are selected from di-, tri- or tetrahalo-phenyl or -biphenyl or mixtures thereof, and preferably, the di-, tri or tetraboronic acid aryl-compounds are selected from di-, tri- or tetraboronic-acid phenyl or -biphenyl or mixtures thereof, which are reacted with each other.

The inventors have found that tetrakis(triphenylphosphine)palladium ($Pd(PPh_3)_3$), in a particular option used as cross-coupling catalyst, decomposes into palladium nanoparticles with a broad particle size distribution at a temperature above 120° C., preferably above 150° C. as illustrated in FIG. 2. The inventors considered that coupling the decomposition of a metal precursor such as a palladium precursor with the in situ catalyzed C—C coupling polymerization reaction leads to the formation of a polymer network to confine the size of the nascent palladium nanoparticles, thus rendering in a composite Pd/PPhen material that can serve as catalyst for further reactions in one step. In this way, palladium first catalyzes the synthesis of the polymer supports and then act as a source of catalytic metal nanoparticles dispersed on the in situ synthesized carrier material.

The catalyst-loaded polyphenylene polymer particles can be used as catalyst in various chemical processes. Examples for the chemical processes are Suzuki coupling reactions, as well as oxidation reactions, preferably as a gas phase reaction.

The Suzuki coupling reaction can be run in biphasic (aqueous and organic) or only in aqueous environments. Solvent systems include toluene, THF, dioxane and dimethylformamide but are not limited to these can also be used.

Additionally, a wide variety of bases can be used in the inventive Suzuki coupling reaction. Most frequently used bases are $K_2CO_3$, KOtBu, $Cs_2CO_3$, $K_3PO_4$, NaOH, $NEt_3$.

After a first reaction cycle, the catalyst can be recycled and it retains its original morphology, and no significant particle growth or aggregation was observed after several catalytic runs. The polymeric PPhen network shows excellent capability to retain the palladium species, which act as catalysts or precursors of smaller palladium active species, within the highly hydrophobic environment of the solid composite material under reaction conditions. This effect mitigates leaching of palladium species to the aqueous reaction media, rendering an easily recoverable and recyclable catalyst.

In order to expand the scope of reaction of the solid polymer supported catalyst, the inventors have also studied the performance of Pd/PPhen in selective oxidation processes, exemplified for both solvent free liquid and gas phase benzyl alcohol oxidation. Liquid phase processes allow for the study on selectivity at different conversions.

Gas phase processes are easily scaled up and can be easily operated in a continuous mode. Therefore, gas phase benzyl alcohol oxidation is interesting for practical application for the new catalysts.

In contrast, Pd/C mainly catalyzed disproportionation, and only 46% selectivity to benzaldehyde when similar conversion was obtained. To the best of the inventor's knowledge, this is the first example that a polymer based catalyst is used in a gas phase plug flow reactor for organic reactions. Continuous gas phase oxidation of benzyl alcohol has also rarely been reported. The good selectivity of Pd/PPhen suggests substantial potential in practical application.

Characterisation and Properties of Inventive Catalysts

The inventors found that, after 20 hours of reaction, the cross-coupling reaction for preparing Pd/PPhen results in a gray solid which can be readily isolated from the reaction media. X-ray diffraction (XRD) shows that PPhen is amorphous while palladium nanoparticles are crystallized as shown in FIG. 3. The density of the Pd/PPhen composite is 1.38±0.01 g/cm$^{-3}$. The palladium loading in the resulting solid is 2.7 wt %, as determined by inductively coupled plasma-atomic absorption spectroscopy. FIG. 4 provides an overview of the structure of the resulting metal-polymer composite. Scanning electron microcopy (SEM) shows irregularly shaped particles with a smooth, highly curved surface. The size and spatial location of the palladium nanoparticles was investigated with high-resolution, tomographic scanning-transmission electron microscopy (HR-STEM tomography).

As illustrated in FIG. 4, the synthetic protocol results in very small palladium nanoparticles, largely in the size range of 0.5-3 nm, evenly distributed throughout the polymer host. Quantification of the 3D-reconstructed tomogram evidenced that the great majority of the palladium nanoparticles (87%) are confined to the polymeric network of the support material. These results indicate that the in situ developed polymer matrix efficiently restricts the growth of the palladium crystals upon decomposition of the metal precursor, stabilizing polymer-confined palladium crystals of sizes down to the sub-nanometer range. The palladium loading in the Pd/PPhen composite can be readily tuned by simply adjusting the amount of Pd(PPh$_3$)$_4$ in the starting reaction media (FIG. 5). Carrying out the reaction at a lower temperature of 100° C. produced a Pd-free polymer solid (FIG. 6), highlighting the importance of rationally combining the kinetics of the C—C coupling reaction and the decomposition of Pd(PPh$_3$)$_4$ to successfully synthesize a highly dispersed Pd/PPhen composite material.

The solid-state $^{13}$C nuclear magnetic resonance ($^{13}$C-NMR) spectrum of the solid shows two signals at 140.3 and 129.6 ppm, which correspond to the connecting and non-connecting carbon atoms of the polyphenylene structure, respectively (FIG. 4g). The thermal and chemical stability of the Pd/PPhen composite were examined by thermal gravimetric analysis (TGA). The material is stable, showing no evident mass loss, up to ca. 400° C. in air and up to 600° C. in argon atmospheres (FIG. 4h). Nitrogen physisorption experiments evidenced a remarkable porosity in the composite material. The BET-equivalent specific surface area amounts 1010 m$^2$/g, of which ca. 10% corresponds to the external surface of the polymer particles. The total pore volume of 0.46 cm$^3$/g results from equal contributions in the micropore (<1.5 nm) and supermicropore (1.5~2 nm) size ranges, confirming the substantial porosity of the polymeric matrix. This porosity provides accessibility to the palladium, as confirmed by the fact that treatments of the Pd/PPhen composite in liquid solutions of H$_2$O$_2$ and HCl resulted in the quantitative leaching of the metal, rendering a Pd-free polymer residue (FIG. 7). The synthesis of the Pd/PPhen composite is completely reproducible even at gram scale. Overall, these characterizations support the structure of the polymer suggested in FIG. 1 and confirm that the synthesized metal Pd/PPhen composite materials, which can be readily dispersed in all common organic solvents (Table 1), display a remarkable porosity and thermal stability, as desired for catalytic applications.

TABLE 1

Dispersion of Pd/PPhen in different solvents.

| Solvent | Dispersion |
|---|---|
| Benzene | Yes |
| Toluene | Yes |
| CH$_2$Cl$_2$ | Yes |
| CH$_3$OH | Yes |
| C$_2$H$_5$OH | Yes |
| Benzene alcohol | Yes |
| acetone | Yes |
| THF | Yes |
| Diglyme | Yes |
| DMF | Yes |
| H$_2$O | No |
| H$_2$O (PVP)[1] | Yes |

[1]10 wt % of PVP is added in order to disperse Pd/PPhen in water.

The metal free PPhen is further used as support to load further metals such as Ru, Cu, Au, Ni, VOx, Pt and Co nanoparticles via impregnation methods. The obtained Pt nanoparticles are in the size range of 0.5-1.5 nm. The obtained Co nanoparticles are in the size range of 4-8 nm as shown in FIG. 8.

Usefulness of the Inventive Catalysts

Surprisingly, the inventors of the present invention have found that a polyphenylene support can serve as an excellent platform for several metal catalyzed reactions, which are typically carried out under homogeneous conditions. Thus, the M/PPhen catalysts of the present invention can be used for a variety of catalytic reactions. Among those, Suzuki C—C coupling reactions are mentioned which are among the most important reactions in organic synthesis. They are mostly carried out in homogeneous phase, catalyzed by palladium complexes such as Pd(PPh$_3$)$_4$, which was employed in this study in the dual role of catalyst for the synthesis of the polyphenylene support and precursor for the palladium nanoparticles in the Pd/PPhen composite. Due to the exclusively aromatic backbone of the polyphenylene carrier, it might be anticipated that application of this material as catalyst in Suzuki coupling reactions could lead to favorable interaction of the substrates of the coupling reactions with the surface of the porous support, in the vicinity of the catalytic palladium nanoparticles.

Initially, the Suzuki coupling reaction between 4-chlorotoluene and phenylboronic acid was carried out to compare the performance of the Pd/PPhen catalyst with conventional Suzuki coupling catalysts. The steric requirements are not very demanding with these reactants, but chloroaromatic compounds are typically very difficult to activate. Pd(PPh$_3$)$_4$ is known to be active for this reaction in organic phase. Similar to its homogeneous counterparts, Pd/PPhen converts 79% of 4-chlorotoluene to 4-methyl-1,1'-biphenyl in an ethanol/water (1:1) mixture within 3 h at a catalyst/substrate ratio of 0.8 mol % (Table 3, entry 1). In addition, pure water was used as solvent instead of volatile organic solvents because it is environmentally more benign and facilitates work-up of the reaction mixture. Polyvinylpyrrolidone (PVP, MW=55,000) was added to the solid catalysts to allow easy dispersion in water. 2.7 wt % Pd/PPhen gives 82% yield of 4-methyl-1,1'-biphenyl in 3 hours (Table 3, entry 2). The use of 5.9 wt % Pd/PPhen results in a lower yield, likely due to the increased palladium nanoparticle size (Table 3, entry 3 and FIG. 5). Such reactivity of the Pd/PPhen solids cannot be attributed to residual Pd(PPh$_3$)$_4$ species. As shown in FIG. 9, solid-state $^{31}$P NMR spectroscopy ruled out the presence of Pd(PPh$_3$)$_4$ in the metal-polymer composite. XRD indicated the presence of crystallized palladium nanoparticles (FIG. 3). In line with these results, the X-ray photoelectron spectra of the Pd/PPhen catalyst shows two signals corresponding to Pd(0) 3 d$_{5/2}$ (335.9 eV) and 3 d$_{3/2}$ (341.2 eV), confirming the metallic character of the metal species responsible for the catalytic activity.

The remarkable catalytic performance afforded by the Pd/PPhen materials contrasted with the poor results obtained under the same reaction conditions by a variety of benchmark catalysts, including soluble metal complexes such as Pd(PPh$_3$)$_4$, and Na$_2$PdCl$_4$, as well as palladium nanoparticles supported on carbon and alternative polymer (polydivinylbenzene, PDVB, which essentially corresponds to the backbone of widely applied Amberlyst catalysts) as solid carriers. The use of Pd(PPh$_3$)$_4$ and Na$_2$PdCl$_4$ metal complexes as catalysts result in no measurable formation of 4-methyl-1,1'-biphenyl in aqueous phase (Table 3, entry 4,5). No trace of the 4-methyl-1,1'-biphenyl product could be detected using a commercial Pd/C as catalyst (Table 3, entry 6).

Due to the relative larger size of palladium nanoparticles in commercial Pd/C (FIG. 10), Pd(PPh$_3$)$_4$, the precursor of Pd/PPhen, was also used for the impregnation ultrasmall palladium nanoparticles on carbon (FIG. 11) (2.7 wt %, size range: 0.5-2.5 nm) and on PDVB (FIG. 11) (2.7 wt %, size range: 0.5-3.5 nm) support materials through impregnation. However, in stark contrast to Pd/PPhen, the resulting Pd/C and Pd/PDVB catalysts are not active (Table 3, entry 7,8).

Hence, the novel Pd/PPhen material displays an exceptional catalytic activity, which is impaired by neither soluble complexes nor palladium nanoparticles, of similar sizes, supported on bench mark carrier materials of similar particle morphology and texture but different chemical nature. This strongly suggests a dominant role of the PPhen support material in the catalytic performance. The strong support effect associated with PPhen may be attributed to the presence of biaryl groups, which are absent in carbon and PDVB and which might allow for strong π-π interactions with the substrates in the vicinity of the catalytic palladium species.

The Pd/PPhen composite shows also a remarkable capacity to retain the catalytic palladium species within the polymeric host matrix, enabling satisfactory recyclability of the catalysts. The nature of the "true" catalytic species in Suzuki coupling reactions has been long debated. Under the experimental conditions chosen by the inventors, removal of the solid catalyst from the reaction media via hot filtration revealed that neither product nor 4-cholortoluene could be detected in the remaining solution (for analysis, reactants and products were extracted. This result evidences the capacity of the PPhen solid carrier to locally provide an organic solvent-like environment for the palladium nanoparticles. When fresh 4-chlorotoluene and phenylboronic acid substrates and base were added into this solid-free solution, along with TBAB to transfer 4-chlorotoluene into the aqueous phase, no reaction was detected after 3 h at 80° C. Elemental analysis of the catalyst-free solution revealed palladium concentrations below 10 ppm. Such resistance to palladium leaching enabled the efficient recycling of the Pd/PPhen catalyst. The recycle efficiency remains between 78% and 84% until the fourth recycling reaction as shown in Table 2.

TABLE 2

Recycling of the Pd/PPhen catalyst for Suzuki coupling reaction $$CH_3-\phantom{xx}-Cl + \phantom{xx}-B(OH)_2 \xrightarrow[NaOCH_3, H_2O]{Pd/PPhen} \phantom{xx}-\phantom{xx}$$

| Recycle times | Yield (%) |
|---|---|
| 0 | 82 |
| 1 | 79 |
| 2 | 82 |
| 3 | 84 |
| 4 | 78 |

In order to expand the scope of reaction of the solid polymer supported catalyst, the inventors have also studied the performance of Pd/PPhen in both solvent free liquid and gas phase benzyl alcohol oxidation. Liquid phase processes allow for the study on selectivity at different conversions. Gas phase processes are easily scaled up and can be easily operated in a continuous mode. Therefore, gas phase benzyl alcohol oxidation could be interesting for practical application.

High selectivity towards benzaldehyde is the most important target in this reaction, which has substantial industrial importance. Side reactions, such as over-oxidation to benzoic acid with subsequent decarboxylation and disproportionation to toluene should be suppressed. In liquid phase, selectivities of benzaldehyde in Pd/PPhen catalyzed reaction are 10-15% higher than those in Pd/C catalyzed reaction at conversions between 20% and 80%. In gas phase, the selectivity was below 50% when using Pd/PPhen at 190° C. and 160° C. Benzene was observed as the main product, which was generated from over-oxidation with subsequent decarboxylation. At 120° C., 47% yield and 79% of selectivity was observed, where both over-oxidation and disproportionation were restricted.

BRIEF DESCRIPTION OF THE DRAWINGS

The invention is further illustrated in the attached Figures. In said Figures, there is shown.

Figure 1:
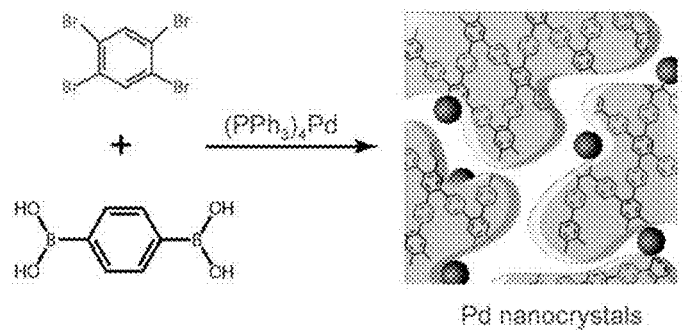
FIG. 1: Scheme for the formation of Pd/PPhen by (Ph$_3$P)$_4$Pd catalyzed coupling of 1,2,4,5-tetrabromobenzene and benzene-1,4-diboronic acid.
Figure 2:
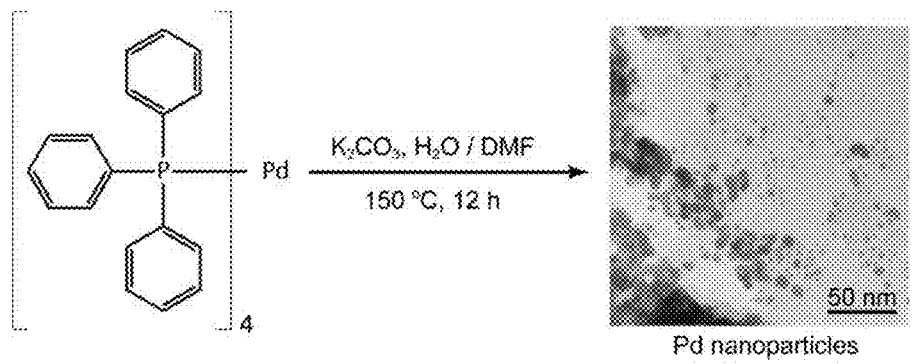
FIG. 2: Reaction condition of palladium precipitation from Pd(PPh$_3$)$_4$, and TEM image of palladium nanoparticles.
Figure 3:
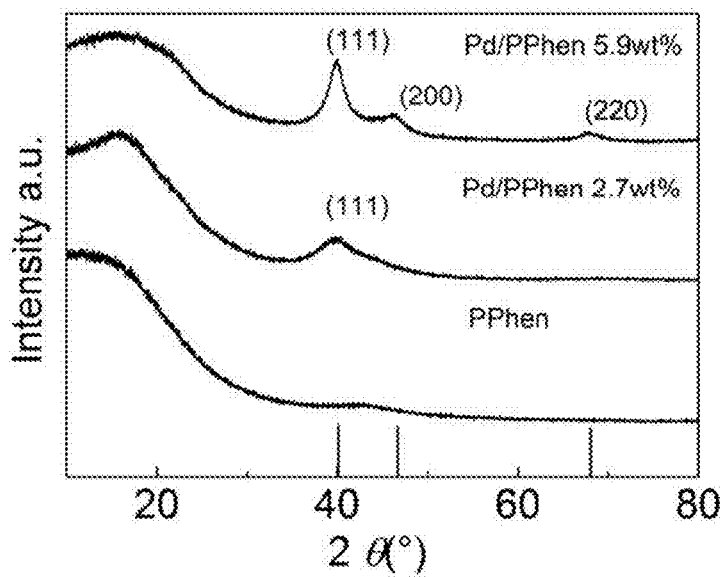
FIG. 3: XRD pattern of 2.7 wt %, 5.9 wt % Pd/PPhen and pure PPhen. The diffraction peaks correspond to palladium crystal.
Figure 4:
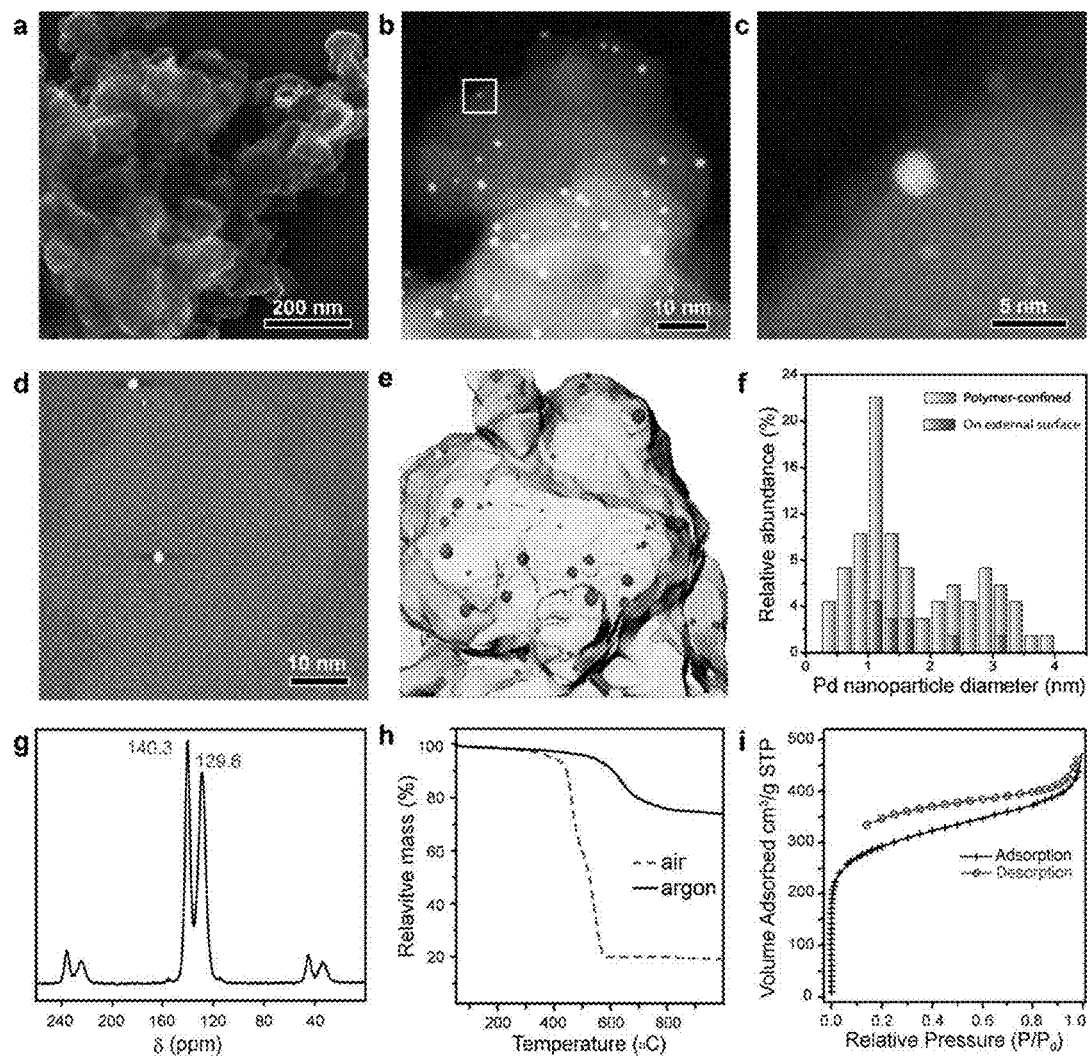
FIG. 4: Structure of Pd/PPhen solid composite.
Figure 5:
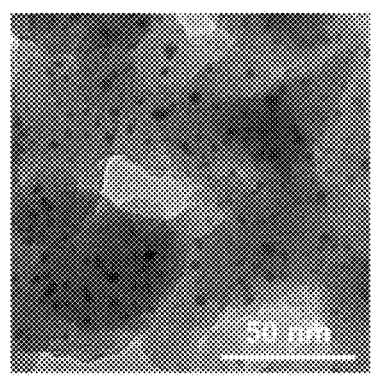
FIG. 5: TEM image of 5.9 wt % Pd/PPhen obtain from 450 mg of Pd(PPh₃)₄ in a single batch reaction.
Figure 6:
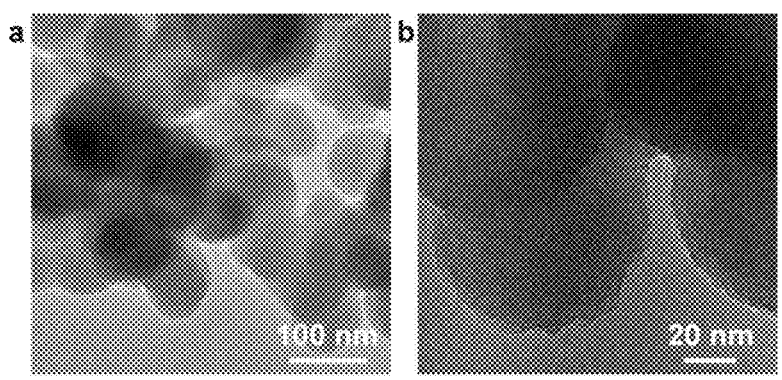
FIG. 6: Pure PPhen obtained at 100° C. a, TEM at large scale. b, TEM at small scale.
Figure 7:
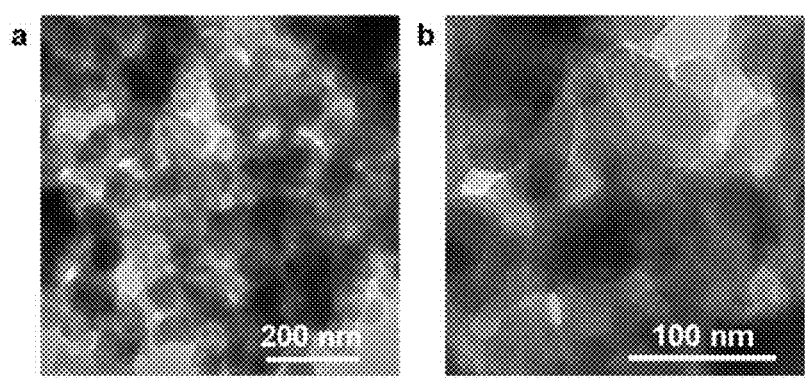
FIG. 7: PPhen after HCl and H₂O₂ treatment. a, TEM image at large scale. b, TEM image at small scale. 5 mg polymer was dispersed in 3 ml HCl (1 M) and reacted with 0.1 mL H₂O₂.
Figure 8:
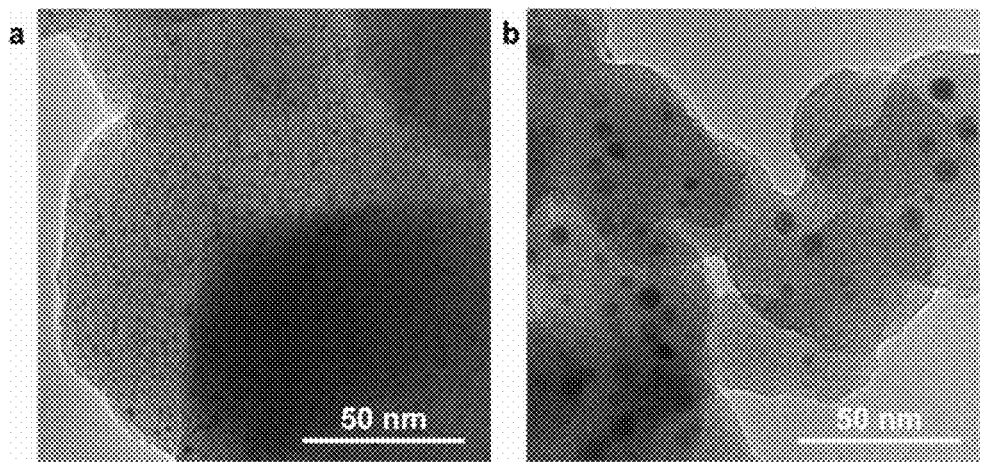
FIG. 8: TEM images of
a: Pt/PPhen, b: Co/PPhen, c: Au/PPhen, d: Ru/PPhen, e: Ni/PPhen, f: VO$_x$/PPhen.
Figure 8:
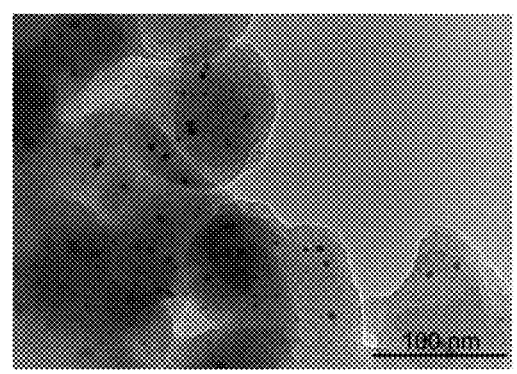
Figure 8D:
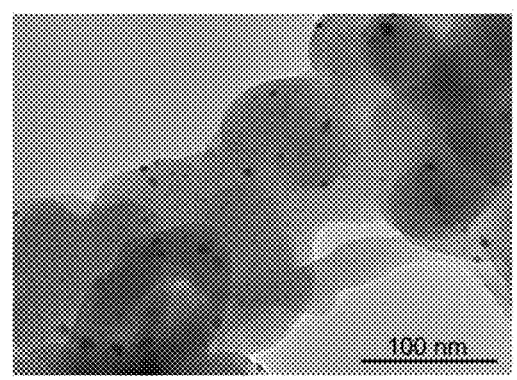
Figure 8E:
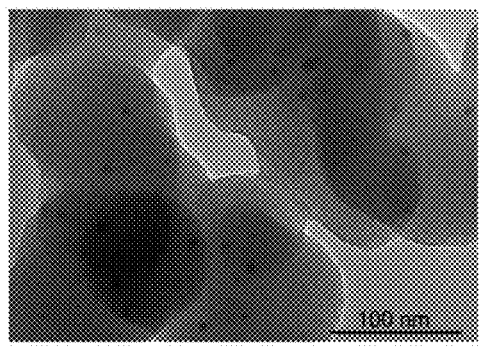
Figure 8F:
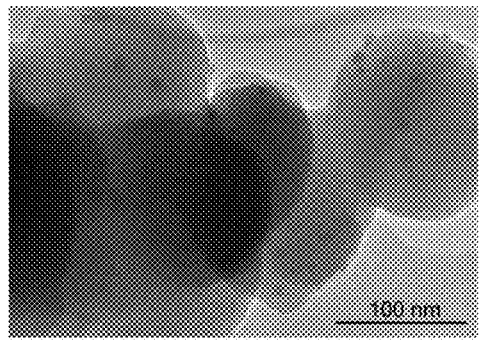
Figure 9:
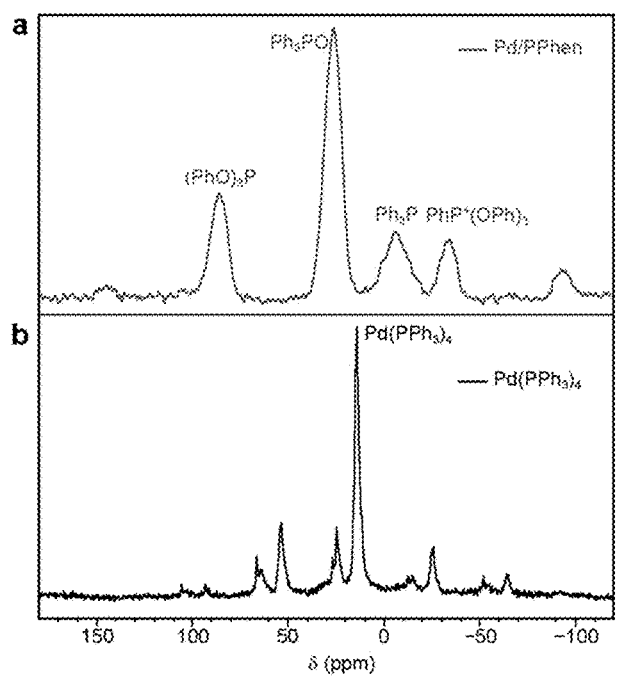
FIG. 9: Solid-state $^{31}$P NMR spectroscopy;
a, Pd/Phen composite. The majority of the phosphor species are Ph₃PO and (PhO)₃P,
b, Pure solid Pd(PPh₃)₄.
Figure 10:
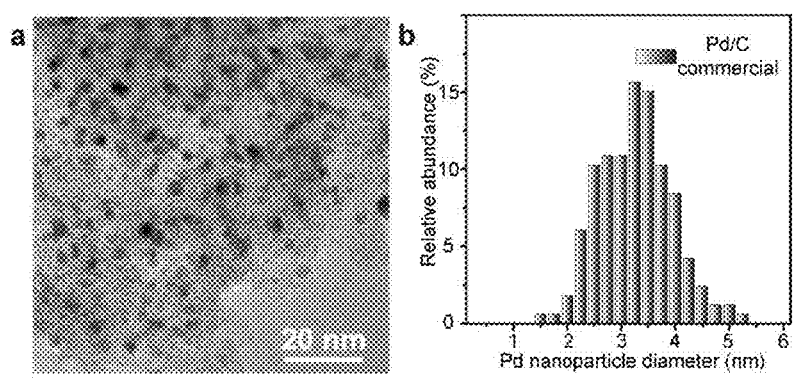
FIG. 10: Pd/C obtained from Sigma. a, TEM image. b, size distribution.
Figure 11:
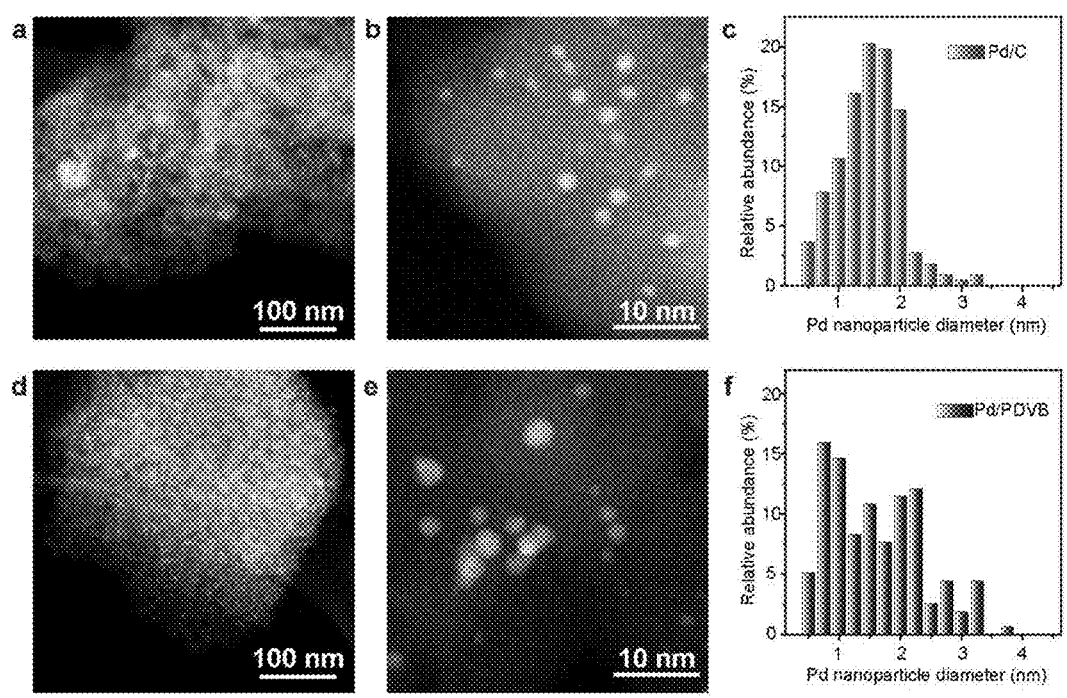
FIG. 11: PHAADF-STEM micrographs of a,b) 2.7 wt % Pd/C and d,e) 2.7 wt % Pd/PDVB catalysts prepared via impregnation of Pd(PPh₃)₄ on the supports followed by thermal decomposition/reduction in flow of 20% H₂/Ar. Palladium particle size distribution of c) 2.7 wt % Pd/C and f) 2.7 wt % Pd/PDVB.
Figure 12:
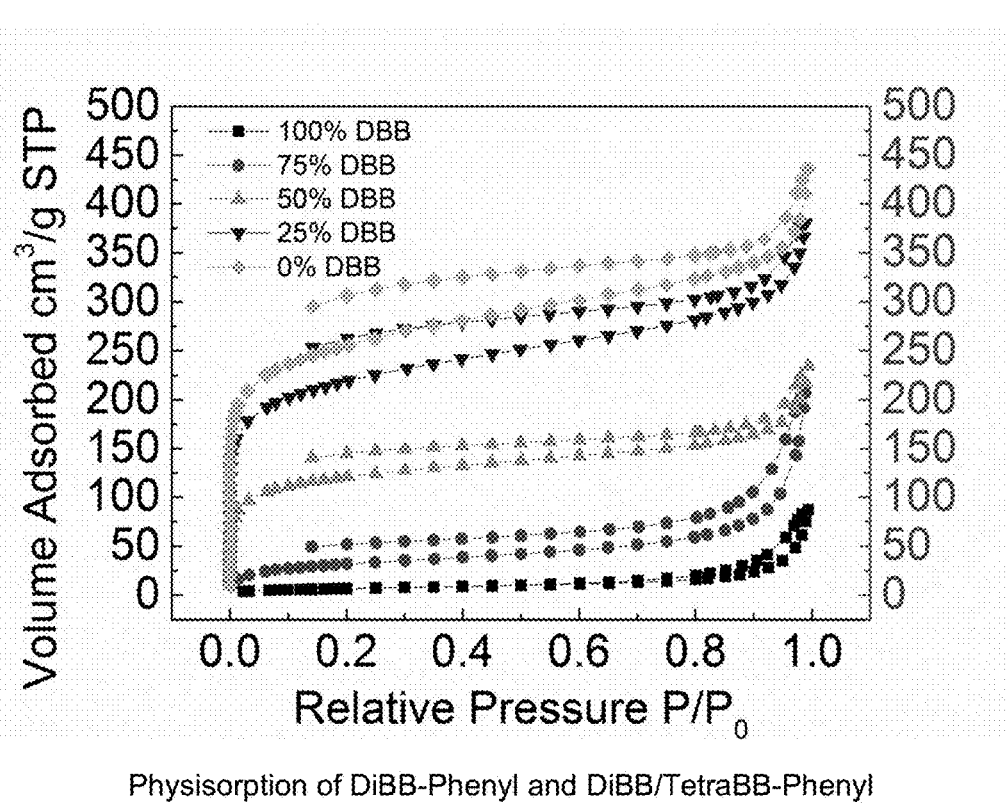
FIG. 12: Graph illustrating the influence of various ratios of DiBB/TetraBB-Phenyl reacted with benzene-1,4-diboronic acid on the adsorption characteristics of the formed product.

The invention is further illustrated in the following Examples.

EXAMPLE 1

Preparation of Metal-Loaded Polyphenylenes

A. TetraBB-Linked Pd/PPhen (TetraBB-Phenyl)

For 2.7 wt % Pd/PPhen, 1,2,4,5-tetrabromobenzene (0.765 g, 1.94 mmol) and benzene-1,4-diboronic acid (0.645 g, 3.89 mmol) are added into 60 mL dimethylformamide. The mixture is degassed through three freeze-pump-thaw cycles. K₂CO₃ (2.0 M, 7.5 mL) and Pd(PPh₃)₄ (0.225 g, 0.19 mmol) are then added with subsequent three freeze-pump-thaw cycles. The mixture is then purged with Ar and heated to 150° C. for 20 h under stirring. The product precipitates in water, and is washed by water, dichloromethane and methanol. Approximately 600 mg of grey product is obtained in each batch.

To obtain 2 g polymer at one batch, all the chemical usages are increased 4 times. The amount of Pd(PPh₃)₄ is changed to 0.450 mg to obtain 5.9 wt % Pd/PPhen. PVP (M$_w$=55,000, 100 mg) is added into the synthesis to make the catalysts dispersible in water. They are then used for further aqueous phase cross-coupling reactions.

2.7 wt % Pd/PPhen can be obtained from 225 mg of Pd(PPh₃)₄ in a single batch reaction. 5.9 wt % Pd/PPhen can be obtained from 450 mg of Pd(PPh₃)₄ in a single batch reaction.

B. DiBB-Linked Pd/PPhen (DiBB-Phenyl)

For Pd/PPhen (100% DBB), 1,4-dibromobenzene (0.458 g, 1.94 mmol) and benzene-1,4-diboronic acid (0.332 g, 1.94 mmol) are added into 30 mL dimethylformamide. The mixture is degassed through three freeze-pump-thaw cycles. K₂CO₃ (2.0 M, 3.75 mL) and Pd(PPh₃)₄ (0.112 g, 0.1 mmol) are then added with subsequent three freeze-pump-thaw cycles. The mixture is then purged with Ar and heated to 150° C. for 20 h under stirring. The product precipitates in water, and is washed by water, dichloromethane and methanol. Approximately 300 mg of grey product is obtained in each batch.

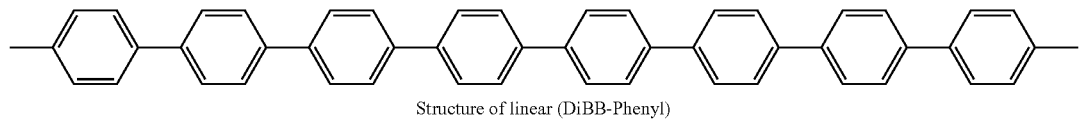

Structure of linear (DiBB-Phenyl)

C. DiBB-TetraBB-Linked Pd/PPhen (DiBB/TetraBB-Phenyl)

For Pd/PPhen with 75%, 50%, 25% DiBB, a mixture of 1,2,4,5-tetrabromobenzenen and 1,4-dibromobenzene are added into 30 mL dimethylformamide together with benzene-1,4-diboronic acid (0.645 g, 3.89 mmol). The molar ratio between 1,2,4,5-tetrabromobenzenen and 1,4-dibromobenzene are 1:3, 2:2 and 3:1 for Pd/PPhen (75%, 50%, 25% DBB) respectively. The mixture is degassed through three freeze-pump-thaw cycles. K₂CO₃ (2.0 M, 7.5 mL) and Pd(PPh₃)₄ (0.225 g, 0.2 mmol) are then added with subsequent three freeze-pump-thaw cycles. The mixture is then purged with Ar and heated to 150° C. for 20 h under stirring. The product precipitates in water, and is washed by water, dichloromethane and methanol. Approximately 600 mg of grey product is obtained in each batch.

D. TriBB-Linked Pd/PPhen (TriBB-Phenyl)

For Pd/PPhen (TriBB), 1,3,5-tribromobenzene (0.816 g, 2.59 mmol) and benzene-1,4-diboronic acid (0.332 g, 1.94 mmol) are added into 30 mL dimethylformamide. The mixture is degassed through three freeze-pump-thaw cycles. K₂CO₃ (2.0 M, 3.75 mL) and Pd(PPh₃)₄ (0.112 g, 0.1 mmol) are then added with subsequent three freeze-pump-thaw cycles. The mixture is then purged with Ar and heated to 150° C. for 20 h under stirring. The product precipitates in water, and is washed by water, dichloromethane and methanol. Approximately 600 mg of grey product is obtained in each batch.

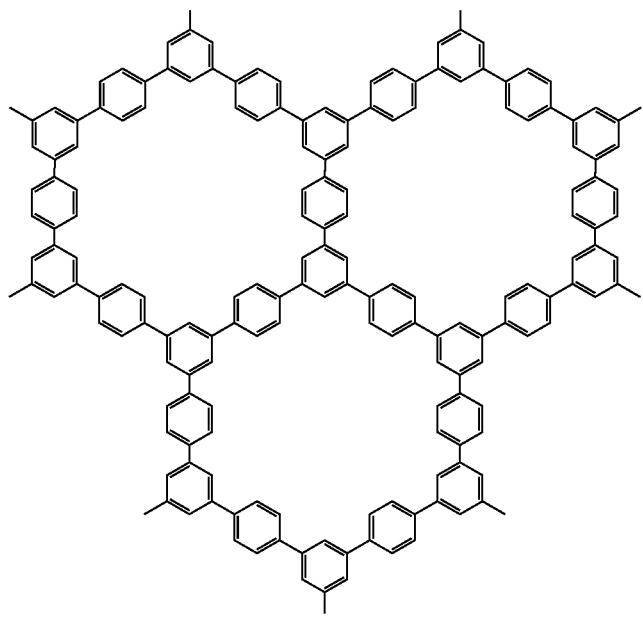

Structure of TriBB-Phenyl

E. TriBB-Linked Pd/PPhen (TriBB-Biphenyl)

For Pd/PPhen (TriBB+Biphenyl), 1,3,5-tribromobenzene (0.079 g, 0.25 mmol) and 4,4-biphenyldiboronic acid benzene-1,4-diboronic acid (0.091 g, 0.375 mmol) are added into 8 mL dimethylformamide. The mixture is degassed through three freeze-pump-thaw cycles. $K_2CO_3$ (2.0 M, 0.75 mL) and $Pd(PPh_3)_4$ (0.025 g, 0.02 mmol) are then added with subsequent three freeze-pump-thaw cycles. The mixture is then purged with Ar and heated to 150° C. for 20 h under stirring. The product precipitates in water, and is washed by water, dichloromethane and methanol. Approximately 50 mg of grey product is obtained in each batch.

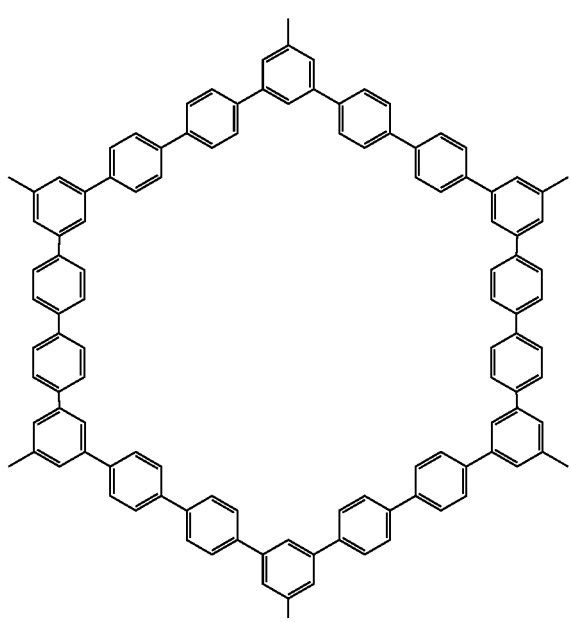

Structure of TriBB-Biphenyl

EXAMPLE 2

Preparation of Metal-Free PPhen

Method 1: First, 1,2,4,5-tetrabromobenzene (0.765 g, 1.94 mmol) and benzene-1,4-diboronic acid (0.645 g, 3.89 mmol) are added into 60 mL dimethylformamide. The mixture is degassed through three freeze-pump-thaw cycles. $K_2CO_3$ (2.0 M, 7.5 mL) and $Pd(PPh_3)_4$ (0.112 g, 0.10 mmol) are then added with subsequent three freeze-pump-thaw cycles. The mixture is then purged with Ar and heated to 100° C. for 12 h under stirring. The product precipitates in water, and is washed by water, dichloromethane and methanol. Approximately 600 mg of a slight yellow product is obtained in each batch.

Method 2: First, a Pd/PPhen is synthesized via the process described in Example 1. Then, pure metal free PPhen can be obtained via $H_2O_2$ and HCl treatments of the 2.7 wt % Pd/PPhen composite in liquid solutions.

EXAMPLE 3

Preparation of Pd/PPhen from PPhen

To synthesize 5 wt % Pd/PPhen, 250 mg $Pd(PPh_3)_4$ or 72 mg Pd acetylacetonate $(Pd(acac)_2)$ is disolved in to 12.5 g of $CH_2Cl_2$. The solution is impregnated into 500 mg of PPhen, with subsequent calcination under 5% $H_2$/Ar at 400° C. for 3 h. The resulted solid in brown. To synthesize Pd/PPhen at other loading, the amount of $Pd(PPh_3)_4$ or $Pd(acac)_2$ is varied.

EXAMPLE 4

Preparation of Other Me/PPhen from PPhen

To synthesize Pt/PPhen, Au/PPhen, Ru/PPhen, Cu/PPhen, Ni/PPhen, Co/PPhen, Fe/PPhen and VO$_x$/PPhen, Pt(acac)$_2$, HAuCl$_4$, Ru(acac)$_3$, Cu(acac)$_2$, Ni(acac)$_2$, Co(acac)$_2$, Fe(acac)$_3$ and VO(acac)$_2$ are used instead of Pd(acac)$_2$ in the procedure of Example 3.

EXAMPLE 5

Suzuki Coupling Reaction Catalyzed by Pd/PPhen

Typically, phenylboronic acid (91.5 mg, 0.75 mmol), sodium methoxide (81.0 mg, 1.5 mmol), 2.7 wt % Pd/PPhen (15.7 mg, 4 μmol) and PVP (M$_w$=55,000, 0.5 mg) are added into 5 mL water. The solution is treated with ultrasound for 0.5 h, and 4-chlorotoluene (63.3 mg, 0.50 mmol) and dodecane (35.0 mg, 0.21 mmol) are added. Dodecane acts as the internal standard. The mixture is degassed through three freeze-pump-thaw cycles, purged with Ar, and stirred at 80° C. for 3 h. Toluene is added into the solution to extract the products.

The products are analyzed by gas chromatography (GC) equipped with flame ionization detector (FID) for quantification. For other Suzuki coupling reactions, the same molar amounts of aryl chloride or arylboronic acid are added instead of 4-chlorotoluene or phenylboronic acid. For the Suzuki coupling reaction with other catalysts, catalysts with the same molar amount of palladium are added instead of Pd/PPhen. For recycling, the catalysts are filtered off, washed with ethanol, dried and weighed, and added into a new reaction mixture with a fixed Pd/4-chlorotoluene ratio of 0.8 mol %.

EXAMPLE 6

Suzuki Coupling Reactions Catalyzed by Pd/PPhen

Similarly, Suzuki coupling reactions catalyzed by the inventive Pd/PPhen as in Example 5 are carried out with other reagents as indicated in Table 3, including a Pd/Phen catalyst material prepared according to U.S. Pat. No. 3,974,095.

TABLE 3

Suzuki coupling reactions using different Pd catalysts, aryl chlorides and arylboronic acids.

$$R_1\text{-C}_6\text{H}_4\text{-Cl} + R_2\text{-C}_6\text{H}_4\text{-B(OH)}_2 \xrightarrow[\text{NaOCH}_3, \text{H}_2\text{O}]{\text{Pd catalysts}} R_1\text{-C}_6\text{H}_4\text{-C}_6\text{H}_4\text{-}R_2$$

| Entry | Aryl chloride | Arylboronic acid | Catalyst | Time (h) | Yield (%) |
|---|---|---|---|---|---|
| 1 | 4-methylphenyl-Cl | phenyl-B(OH)$_2$ | Pd/PPhen 2.7 wt % in C$_2$H$_5$OH/water | 3 | 82 |
| 2 | 4-methylphenyl-Cl | phenyl-B(OH)$_2$ | Pd/PPhen 2.7 wt % | 3 | 82 |
| 3 | 4-methylphenyl-Cl | phenyl-B(OH)$_2$ | Pd/PPhen 5.9 wt % | 3 | 27 |
| 4 | 4-methylphenyl-Cl | phenyl-B(OH)$_2$ | Pd(PPh$_3$)$_4$† | 3 | n.d. |
| 5 | 4-methylphenyl-Cl | phenyl-B(OH)$_2$ | Na$_2$PdCl$_4$† | 3 | n.d. |
| 6 | 4-methylphenyl-Cl | phenyl-B(OH)$_2$ | Pd/C from Sigma Aldrich | 3 | n.d. |
| 7 | 4-methylphenyl-Cl | phenyl-B(OH)$_2$ | Pd/C‡ | 3 | n.d. |
| 8 | 4-methylphenyl-Cl | phenyl-B(OH)$_2$ | Pd/PDVB‡ | 3 | n.d. |

TABLE 3-continued

Suzuki coupling reactions using different Pd catalysts, aryl chlorides and arylboronic acids.

| Entry | Aryl chloride | Arylboronic acid | Catalyst | Time (h) | Yield (%) |
|---|---|---|---|---|---|
| 9 | 2,6-dimethylphenyl-Cl | phenyl-B(OH)$_2$ | Pd/PPhen 2.7 wt % | 3 | 55 |
| 10 | 4-H$_3$CO-phenyl-Cl | phenyl-B(OH)$_2$ | Pd/PPhen 2.7 wt % | 3 | 20 |
| 11 | 4-H$_3$CO-phenyl-Cl | phenyl-B(OH)$_2$ | Pd/PPhen 2.7 wt % | 20 | 80 |
| 12 | 2,6-dimethylphenyl-Cl | 2-methylphenyl-B(OH)$_2$ | Pd/PPhen 2.7 wt % | 3 | 51 |
| 13 | 2,6-dimethylphenyl-Cl | 2-methylphenyl-B(OH)$_2$ | Pd/PPhen 2.7 wt % | 20 | 87 |
| 14 | 4-methylphenyl-Cl | phenyl-B(OH)$_2$ | Pd/PPhen (25% DiBB) 2.7 wt % | 3 | 32 |
| 15 | 4-methylphenyl-Cl | phenyl-B(OH)$_2$ | Pd/PPhen (50% DiBB) 2.7 wt % | 3 | 43 |
| 16 | 4-methylphenyl-Cl | phenyl-B(OH)$_2$ | Pd/PPhen (75% DiBB) 2.7 wt % | 3 | 24 |
| 17 | 4-methylphenyl-Cl | phenyl-B(OH)$_2$ | Pd/PPhen (10% DiBB) 2.7 wt % | 3 | 13 |
| 18 | 4-methylphenyl-Cl | phenyl-B(OH)$_2$ | Pd/PPhen according to U.S. Pat. No. 3,974,095 (Pd 2.7 wt %) | 3 | 5 |

*Reaction conditions unless otherwise indicated: aryl chloride 0.5 mmol, arylboronic acid 0.75 mmol, NaOCH$_3$ 1.5 mmol, catalyst (0.8 mol % Pd to aryl chloride), PVP 0.5 mg, water 5 mL, 80° C., under argon.
†Tetrabutylammonium bromide (TBAB) 0.3 mmol is added as phase transfer catalyst.
‡Pd/C and Pd/PDVB here are prepared by impregnation using active carbon or PDVB and P(PPh$_3$)$_4$ with subsequent calcination under H$_2$/Ar at 250° C. for 3 h.
n.d.: not detectable.

These results of Table 3 show the superiority of the Pd/PPhen catalyst over all other systems studied. In homogeneous catalysis, Pd(PPh$_3$)$_4$ is reactive enough for activated (hetero)aryl chlorides in nonaqueous solution. However, more effective ligands, such as N-heterocyclic carbenes, P(tBu)$_3$ or the phosphine family developed by Buchwald and co-workers, are required for palladium complexes to catalyze Suzuki coupling reactions involving unactivated aryl chlorides, such as chlorotoluene, 2-chloro-1,3-dimethylbenzene or 4-chloroanisole owing to their low intrinsic reactivity, which relates to steric effects of the substituents and the electron donating effect for oxidative addition. These substrates are known to pose an even greater challenge to heterogeneous catalysis. Interestingly, similar to Buchwald ligands, polyphenylene also contains biaryl substructures, which provide a similar environment for the catalytic Pd species in the Pd/PPhen solid composite. Indeed, under relevant reaction conditions, the application of Pd/PPhen as catalyst in the Suzuki coupling reaction of 2-chloro-1,3-dimethylbenzene with arylboronic acid results in a reaction yield above 50% after only three hours (Table 3, entry 9). Reaction yields exceeding 80% are obtained for different unactivated substrates after 20 h (Table 3, entry 11, 13). The results indicate that PPhen may act as a ligand to stabilize the transition state of the oxidative addition and/or reductive elimination. Transformation from $Pd(PPh_3)_4$ to Pd/PPhen enables reactions that are impossible for $Pd(PPh_3)_4$ itself. This discovery suggests that careful support engineering allows for catalytic reactions that have previously been inaccessible for solid catalysts.

EXAMPLE 7

Solvent-Free Benzyl Alcohol Oxidation in a Batch Setup

Typically, benzyl alcohol (10.4 g, 0.096 mol) and Pd/PPhen (10 mg, 2.5 μmol) or Pd/C are added into a glass inset inside a stainless steel autoclave reactor. The reactor is purged with $O_2$ and kept under 5 bar $O_2$. The product is analyzed by GC-FID using dodecane as standard.

EXAMPLE 8

Benzyl Alcohol Oxidation in a Plug Flow Reaction

Pd/PPhen (20 mg) is mixed with quartz sand (200 mg), and packed into a tube reactor (6 mm×160 mm). An evaporator for benzyl alcohol is connected to the top of the tube reactor. The temperatures of evaporator and reactor are controlled by individual tube ovens. Benzyl alcohol (0.1 ml·h$^{-1}$) is injected through a syringe pump into the evaporator and carried by $O_2$ (50 mL·min$^{-1}$) into the reactor. The partial pressure of benzyl alcohol is controlled to be lower than its vapor pressure. The products are collected in a dry-ice cooled tetrahydrofuran solution with a gas outlet to atmosphere. The solutions are analyzed by GC-FID in one hour intervals with dodecane as standard. The results are shown in Table 4.

TABLE 4

Plug flow benzyl alcohol oxidation.

| Catalysts | Temperature (° C.) | Benzaldehyde yields (%) | Conversion (%) | Selectivity (%) |
| --- | --- | --- | --- | --- |
| Pd/PPhen | 190 | 25 | 84 | 29 |
| Pd/PPhen | 160 | 33 | 80 | 43 |
| Pd/PPhen | 120 | 47 | 59 | 79 |
| Pd/C | 120 | 12 | 23 | 46 |

Reaction conditions: Benzyl alcohol rate 0.1 mL · h$^{-1}$, $O_2$ flow rate 50 mL · min$^{-1}$, Pd/PPhen 2.7 wt % catalyst 20 mg, Pd/C 5 wt % 4 mg, the products are collected between 3rd and 4th hour on-stream.

Analysis Methods

TEM and HAADF-STEM imaging were carried out on an FEI Titan 80-300ST field-emission-gun (FEG) TEM operated at 30 kV. Electron tomography was performed by collecting tilt-series of HAADF-STEM images over a tilt range of −70° to +75° with a tilt increment of 2°. Alignment of the tilt series was performed using a collection of palladium nanoparticles (2-3.5 nm), indigenous to the Pd/PPhen composite, as fiducial markers. Tomogram reconstruction was carried out using a weighted back-projection algorithm in IMOD. Segmentation and 3D visualization of the different phases in the reconstructed volume was performed in Avizo (FEI, The Netherlands). SEM imaging was performed on a Hitachi S-5500 FEG SEM. XRD measurement was performed on a Stoe STADI P Bragg-Brentano diffractometer with Cu $K\alpha_{1,2}$ radiation, using a secondary graphite monochromator. $N_2$ adsorption isotherm was measured on Micromeritics ASAP 2010 adsorption analyzer at 77 k after activation in vacuum at 250° C. for 24 h. XPS analyses were performed on a Kratos HSi spectrometer with a hemispherical analyzer. The monochromatized Al Kα X-ray source (E=1486.6 eV) was operated at 15 kV and 15 mA. An analyzer pass energy of 40 eV was applied for the narrow scans. The hybrid mode was used as lens mode. The base pressure during the experiment in the analysis chamber was $45 \times 10^{-7}$ Pa. All spectra were charge corrected referred to the C1 s photopeak at 284.5 eV. TG measurements were performed on a Netzsch STA 449C thermal analyzer with a heating rate of 10° C. min$^{-1}$. The solid-state NMR spectra were recorded on a Bruker Avance 500WB spectrometer using a double-bearing standard MAS probe (DVT BL4) at resonance frequencies of 125.8 MHz and 202.5 MHz for 13C and 31P, respectively. High-power proton decoupling (CW) and spinning rates between 10 and 12 kHz were applied for all spectra. Density of PPhen was measured on Micromeritics Accupyc 1330 gas pycnometer.

SUMMARY

As shown above, the catalysts of the present invention show excellent activity in the coupling of 1,3-dimethyl-2-chlorobenzene with 2-tolylboronic acid, a reaction which represents a serious challenge even for molecular catalysts under homogeneous reaction conditions. The catalysts also show high selectivity in both liquid and gas phase aerobic oxidation. Thus, the polyphenylene support shows the huge potential as an organic catalysis platform to perform organic reactions that are currently inaccessible with heterogeneous catalysis.

A polyphenylene based solid catalyst platform has been developed for metal catalyzed reactions which are typically performed in homogeneous phase. The Pd/PPhen catalyst, synthesized through the rational coupling of the C—C coupling reaction and the decomposition of $Pd(PPh_3)_4$, shows exceptional catalytic activities in aqueous phase Suzuki coupling reactions using unactivated substrates, such as 1,3-dimethyl-2-chlorobenzene and 4-chloroanisole. The PPhen support, consisting of aromatic rings, can serve as a solid organic solvent and provides the local organic reaction environment. The PPhen support also shows a synergistic effect for Suzuki coupling reactions, as confirmed by the control experiments using conventional catalysts, such as carbon and PDVB supported palladium nanoparticle, which have the same size ranges with that of Pd/PPhen.

The Pd/PPhen catalysts show a remarkable capacity to retain the catalytic palladium species, enabling good recyclability. In addition, high selectivity from benzyl alcohol to benzaldehyde was obtained using Pd/PPhen at both liquid and gas phase. PPhen shows its potential as an organic catalysis platform to enable various organic reactions that are currently inaccessible by heterogeneous catalysis.

The invention claimed is:
1. Catalyst-loaded polyphenylene polymer particles having nanoparticles of catalytically active material dispersed in a polymer network, said nanoparticles having a particle size from 0.25 to 10 nm and the catalytically active material being selected from the group consisting of metals selected from Ti, V, Cr, Mn, Fe, Co, Ni, Cu, Zn, Al, Mo, Se, Sn, Pt, Ru, Pd, W, Ir, Os, Rh, Nb, Ta, Pb, Bi, Au, Ag, Sc, Y and alloys thereof, and compounds thereof wherein said compounds are selected from oxides, phosphides, nitrides and sulfides, wherein said polyphenylene polymer particles are obtainable by a Suzuki coupling reaction of di-, tri or tetrahalo-aryl compounds or mixtures thereof with di-, tri- or tetraboronic acid aryl-compounds or mixtures thereof, wherein said nanoparticles are present from 0.25 to 15%-by weight based on the total weight of the polymer.

2. Catalyst-loaded polyphenylene polymer particles particles according to claim 1, wherein the nanoparticles of the catalytically active material dispersed in the polymer network have a particle size from 0.25 to 5 nm.

3. Catalyst-loaded polyphenylene polymer particles according to claim 1, wherein the catalytically active material is a metal is selected from the group consisting of Co, Ni, Pt, Ru, Pd, Ag, Au and alloys thereof.

4. Catalyst-loaded polyphenylene polymer particles according to claim 1, wherein said nanoparticles are present from 2.5 to 10%-by weight based on the total weight of the polymer.

5. Catalyst-loaded polyphenylene polymer particles according to claim 1, wherein the catalyst-loaded polyphenylene polymer particles are obtainable by a Suzuki coupling reaction of a halogen-aryl compound selected from the group consisting of di-, tri and tetrahalo-aryl compounds with a boronic acid-aryl selected from the group consisting of di-, tri and tetraboronic acid-aryl compounds in the presence of a palladium compound and a base, whereby the molar ratio of the halogen-aryl compound to the boronic acid-aryl compound is in the range of 2.5:1.0 to 1.0:2.5 and wherein the metal is Pd.

6. Process for preparing catalyst-loaded polyphenylene polymer particles of claim 5, said process comprising reacting a halogen-aryl compound selected from the group consisting of di-, tri and tetrahalo-aryl compounds or mixtures thereof with a boronic acid-aryl compound selected from the group consisting of di-, tri and tetraboronic acid-aryl compounds or mixtures thereof in the presence of a palladium compound and a base in a temperature range of 130° C. to 250° C. in a Suzuki coupling reaction whereby the molar ratio of the halogen-aryl compound to the boronic acid-aryl compound is in the range of 2.5:1.0 to 1.0:2.5.

7. Process for preparing catalyst-loaded polyphenylene polymer particles according to claim 6, wherein said di-, tri or tetrahalo-aryl-compounds are selected from di-, tri- or tetrahalo-phenyl or -biphenyl compounds or mixtures thereof.

8. Process for preparing catalyst-loaded polyphenylene polymer particles according to any of claim 6, wherein said di-, tri or tetraboronic acid aryl-compounds are selected from di-, tri- or tetraboronic-acid phenyl or -biphenyl compounds or mixtures thereof.

9. Process for preparing catalyst-loaded polyphenylene polymer particles according to any of claim 6, wherein di-, tri or tetrabromophenyl or -biphenyl compounds or mixtures thereof are reacted with di-, tri or tetraboronic phenyl or -biphenyl compounds or mixtures thereof.

10. Catalyst-loaded polyphenylene polymer particles obtainable by a process comprising treating the catalyst-loaded polyphenylene polymer particles obtainable according to the process of claim 6 by an oxidative leaching whereby the Pd metal is removed and the obtained metal-free polyphenylene polymer particles are impregnated with a solution of a metal compound and evaporating the solvent.

11. A process comprising carrying out a chemical reaction in the presence of a catalyst, wherein the catalyst comprises catalyst-loaded polyphenylene polymer particles as claimed in claim 1, wherein the catalytically active material is a metal is selected from Ti, V, Cr, Mn, Fe, Co, Ni, Cu, Zn, Al, Mo, Se, Sn, Pt, Ru, Pd, W, Ir, Os, Rh, Nb, Ta, Pb, Bi, Au, Ag, Sc, Y or alloys thereof, or compounds thereof wherein said compounds are selected from oxides, phosphides, nitrides or sulfides.

12. Process according to claim 11, wherein the chemical reaction is a Suzuki coupling reaction, or an oxidation reaction.

13. Process according to claim 11, wherein said catalyst-loaded polyphenylene polymer particles are recycled from a catalytic process.

14. Catalyst-loaded polyphenylene polymer particles having nanoparticles of catalytically active material dispersed in a polymer network, said nanoparticles having a particle size from 0.25 to 10 nm and the catalytically active material being selected from the group consisting of palladium and alloys thereof, and compounds thereof wherein said compounds are selected from oxides, phosphides, nitrides and sulfides, wherein said polyphenylene polymer particles are obtainable by a Suzuki coupling reaction of di-, tri or tetrahalo-aryl compounds or mixtures thereof with di-, tri- or tetraboronic acid aryl-compounds or mixtures thereof, wherein said nanoparticles are present from 0.25 to 15%-by weight based on the total weight of the polymer.

15. Catalyst-loaded polyphenylene polymer particles particles according to claim 14, wherein the catalytically active material is Pd.

16. Catalyst-loaded polyphenylene polymer particles according to claim 15, wherein said nanoparticles are present from 2.5 to 10%-by weight based on the total weight of the polymer.

17. A process comprising carrying out a chemical reaction in the presence of a catalyst, wherein the catalyst comprises catalyst-loaded polyphenylene polymer particles as claimed in claim 14.

18. Process according to claim 17, wherein the chemical reaction is a Suzuki coupling reaction, or an oxidation reaction.

19. Process according to claim 17, wherein said catalyst-loaded polyphenylene polymer particles are recycled from a catalytic process.

* * * * *